United States Patent [19]

Arin et al.

[11] 4,078,894
[45] Mar. 14, 1978

[54] ANALYZER SYSTEM WITH SALT EXTRACTOR

[75] Inventors: M. Louis Arin, Lexington, Mass.; Kenneth W. Sweeney, Warwick; John R. Ims, Portsmouth, both of R.I.

[73] Assignee: Raytheon Company, Lexington, Mass.

[21] Appl. No.: 741,168

[22] Filed: Nov. 12, 1976

[51] Int. Cl.² ............................................. G01N 31/12
[52] U.S. Cl. ............................................... 23/253 PC
[58] Field of Search ...................... 23/253 PC, 230 PC

[56] References Cited

U.S. PATENT DOCUMENTS

| | | | |
|---|---|---|---|
| 3,682,598 | 8/1972 | Kaartinen | 23/253 PC X |
| 3,854,881 | 12/1974 | Cohen | 23/253 PC |
| 3,964,868 | 6/1976 | DiCola | 23/230 PC X |

Primary Examiner—Robert M. Reese
Attorney, Agent, or Firm—Daivd M. Warren; Milton D. Bartlett; Joseph D. Pannone

[57] ABSTRACT

A system for analyzing a material such as sewage, the system including a preprocessor for extracting volatile compounds of carbon from inorganic carbonaceous substances within the material, a high-temperature reactor wherein the material chemically reacts with a gaseous reagent to produce a measurable amount of a gaseous product, and a chamber positioned at an exit port of the reactor, the chamber having a liquid covered surface to separate precipitates from the gaseous product.

5 Claims, 2 Drawing Figures

4,078,894

ANALYZER SYSTEM WITH SALT EXTRACTOR

BACKGROUND OF THE INVENTION

This invention relates to an analyzer system having a reactor for high temperature chemical reactions, and more particularly, to a separator of precipitate products from gaseous products of the high temperature reaction.

A high temperature reactor is disclosed in the U.S. Pat. No. 3,964,868 for an Organic Carbon Analyzer System which issued June 22, 1976 in the names of L. S. DiCola, D. W. Kemp and H. D. Evans. The patent discloses the preprocessing of sewage by the addition of acid to extract carbon dioxide from inorganic carbonaceous substances in the sewage, the sewage then being reacted with an oxidant in a high temperture reactor to produce carbon dioxide from organic carbonaceous substances within the sewage.

A problem arises in that a system, such as that of the aforementioned patent which treats sewage and other matter which may have a wide variety of constituents, produces unwanted by-products in the form of salts which precipitate from the high temperature chemical reaction of the system. For example, with reference to the system of the foregoing patent, it has been observed that a salt precipitate is obtained when the temperature of the reactants and their products drops below approximately 800° C. Unfortunately, these precipitates adhere to the portions of the interior surfaces of the equipment where the lower temperatures are found. In time, the extent of the precipitates is sufficient to clog the equipment necessitating shutdown of the system for cleaning.

SUMMARY OF THE INVENTION

The foregoing problem is overcome and other advantages are provided by a system for analyzing a material, such as sewage, the system including a preprocessor for extracting volatile compounds of carbon from inorganic carbonaceous substances within the material. In accordance with the invention, the system includes a high temperature reactor having an exit port positioned in a chamber having a surface covered with a movable material such as a liquid, preferably water. Chemical reactions between the material and a gaseous reagent take place in the reactor at elevated temperatures to produce a gaseous product and a precipitate product, the precipitate being formed as the gaseous product cools in the chamber, the precipitate being absorbed in the material covering the surface of the chamber whereupon it is carried away. In a preferred embodiment of the invention, a bottom surface of the chamber is covered with water which is made to circulate in a closed path which precludes the admission of foreign substances, other than the precipitates, into the water.

BRIEF DESCRIPTION OF THE DRAWINGS

The aforementioned aspects and other features of the invention are explained in the following description taken in connection with the accompanying drawings wherein.

DESCRIPTION OF THE PREFERRED EMBODIMENT

Figure 1:
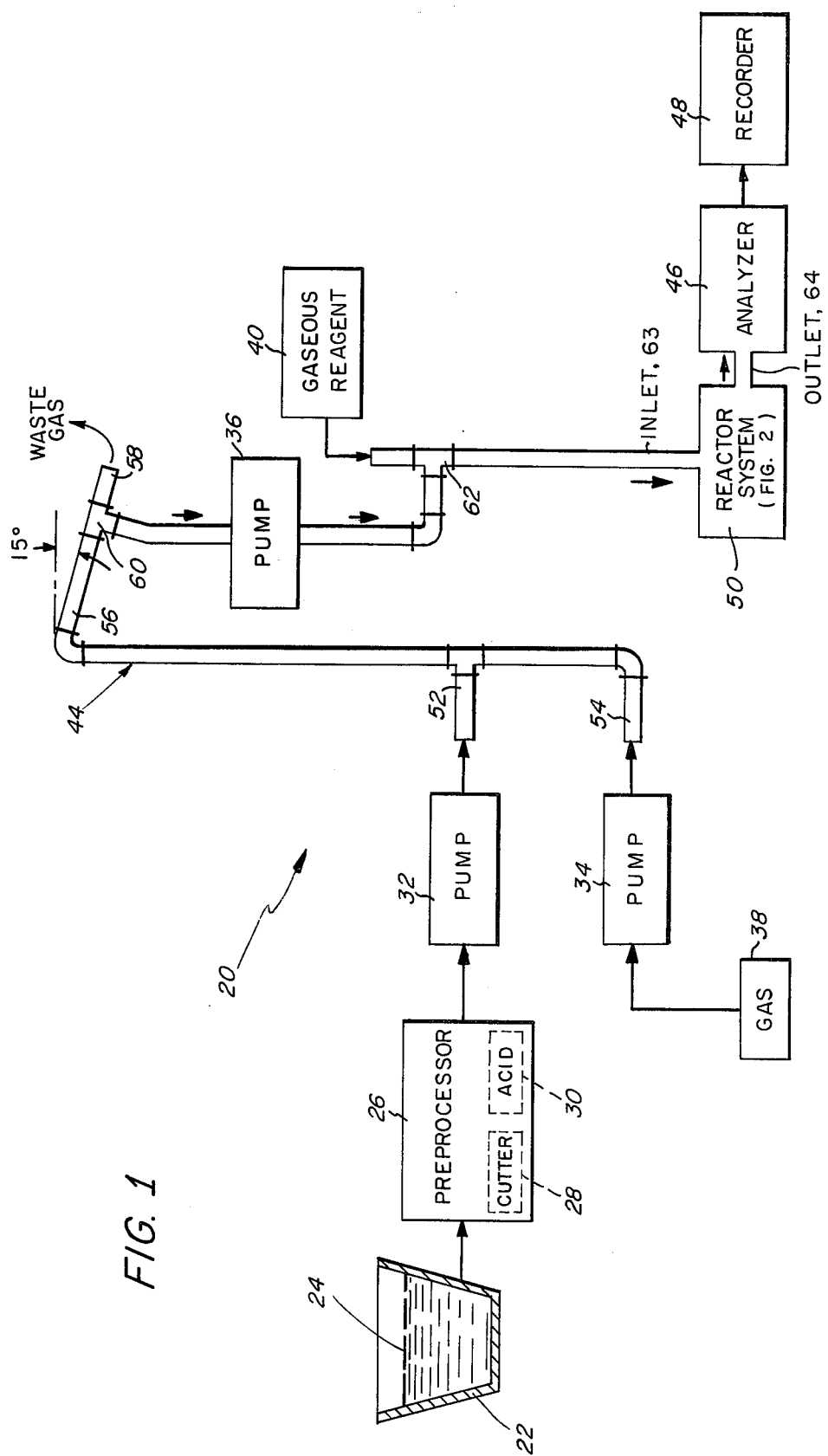
FIG. 1 is a block diagram of an analyzer system incorporating the invention.
Figure 2:
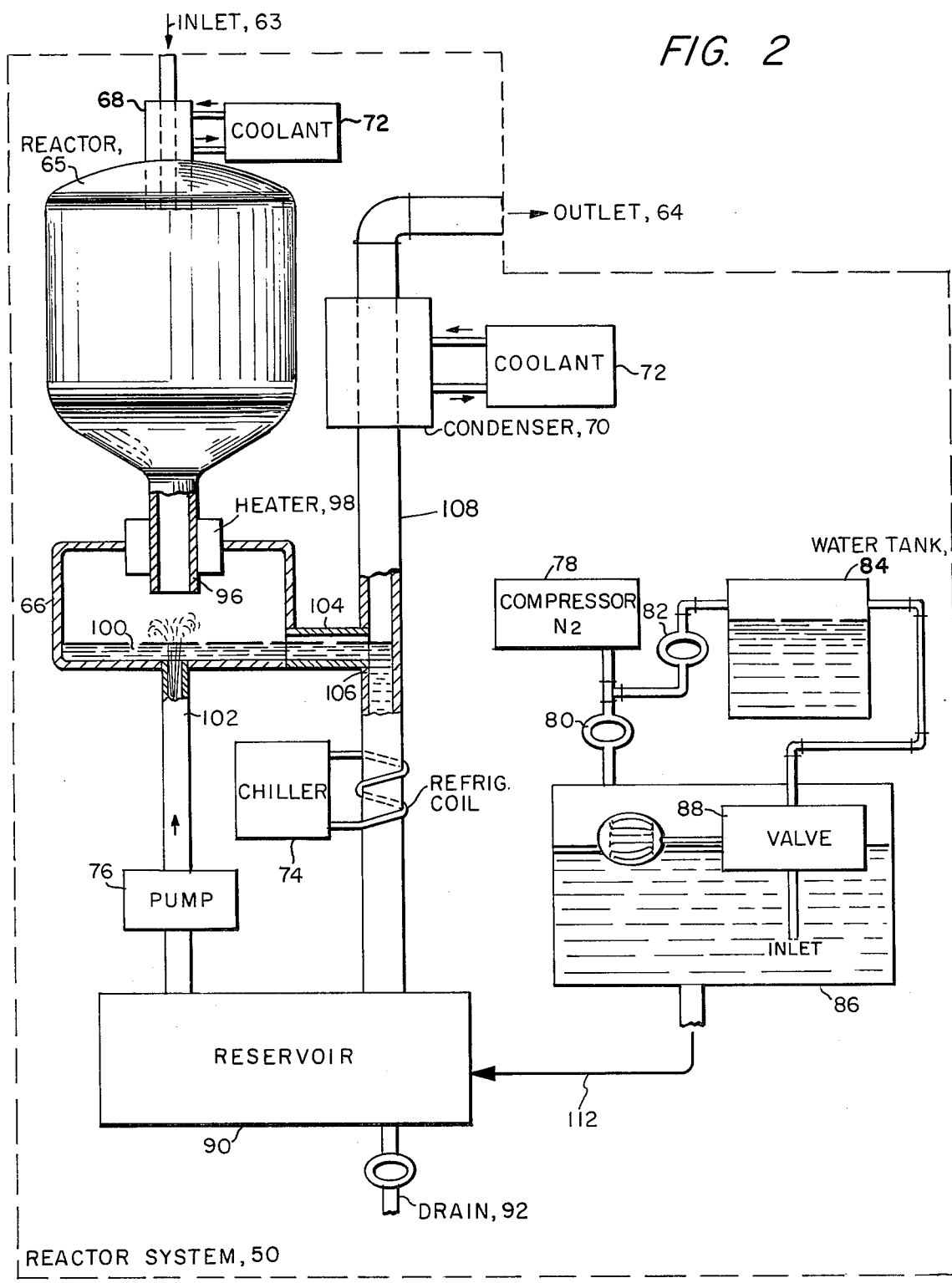
FIG. 2 is a block diagram of a reactor system of FIG. 1 showing a cooling chamber of the invention coupled to an exit port of a reactor.

Referring now to FIG. 1, there is seen a system 20 for the analysis of a liquid such as sewage, the system 20 comprising components described in FIGS. 2 and 5 of the aforementioned patent of DiCola et al. The system 20 comprises a holding tank 22 having sewage 24 therein, a preprocessor 26 including a cutter 28 for cutting sewage material into small particles and an acidifying unit 30 for reacting an acid with the sewage 24, pumps 32, 34 and 36, gas sources 38 and 40, an aerator 44, an analyzer 46, a recorder 48, and a reactor system 50 which incorporates the invention.

In operation, the preprocessor 26 processes the sewage 24 by cutting solid matter therein to small particles which can be transported through the aerator 44, and also applies acid to the sewage 24 for reacting therewith to release carbon dioxide from inorganic carbonaceous substances contained within the sewage. The pump 32 pumps the sewage at a predetermined rate into an upper inlet 52 of the aerator 44 while the pump 34 pumps a gas at a predetermined rate from the source 38 into a lower inlet 54 of the aerator 44, the gas rising in the aerator 44 past the upper inlet 52 whereupon bubbles of gas are formed in the sewage, the bubbles lifting the sewage through the elongated tube of the aerator 44. The gas of the source 38 is free of carbon dioxide, air without carbon dioxide or nitrogen being a suitable gas, so that the carbon dioxide resulting from the acidification can be adsorbed into the gas. The top portion 56 of the aerator 44 is inclined downwardly, for example at an angle of 15°, to allow the waste gas to exit from an outlet 58 while the sewage, free of the carbon dioxide, advances via a tee 60 to the pump 36. The pump 36 pumps the sewage at a predetermined rate to a tee 62 where the sewage mixes with an oxidant, such as oxygen, from the source 40. Droplets of sewage mixed with the oxygen enter the inlet 63 to the reactor system 50 wherein, at a high temperature in the range of 850° to 1000° C, the sewage reacts with the oxidant to produce carbon dioxide from organic carbonaceous substances in the sewage, the carbon dioxide passing from the outlet 64 of the reactor system 50 to the analyzer 46. The analyzer 46 measures the concentration of the carbon dioxide from the reactor system 50 to provide on the recorder 48 a record of the concentration of the carbon dioxide.

Referring now to FIG. 2, there is seen a diagram of a reactor 65 and a separation chamber 66, the latter shown in section, for separating gaseous products from precipitate products of the aforementioned chemical reaction between the sewage and the oxidant, this chemical reaction taking place within the reactor 65. The system 50 comprises condensers 68 and 70 sources 72 of a coolant such as water, a chiller 74, a pump 76, a source 78 of compressed nitrogen, valves 80 and 82, tanks 84 and 86, a float valve 88, and a reservoir 90 having a drain 92.

The mixture of the oxidant gas and the droplets of sewage at the inlet 63 are maintained at a relatively low temperature as compared to the temperature within the reactor 65, by the condenser 68 and the cooling water circulated therein by the source 72 so that no chemical reaction takes place between the sewage and the oxidant until such time as the sewage and the oxidant have entered within the high temperature region of the reactor 65. This prevents a premature reaction between the sewage and the oxidant with the attendant possibility of forming a precipitate along the inlet 63 with a subsequent clogging thereof.

Since the precipitate products, particularly sodium chloride, tend to solidify at temperatures below approximately 800° C, by maintaining all portions of the reactor 65 at a temperature above 800° C, the formation of clogging precipitates upon the interior of the reactor 65 is avoided. The formation of the interior portions of the reactor 65, and the heating thereof to the afore-mentioned high temperatures are described in the aforementioned patent to DiCola et al. In a preferred embodiment of the invention, the reactor 65 was composed of a ceramic, alumina, with alumina balls therein for distributing the heat uniformly throughout the gaseous reagents; the central portion of the reactor 65 measures 2 inches in diameter by 3 inches in length, and the sewage flow therein is 0.1cc/minute while the oxidant, oxygen, flows at a rate of 270cc/minute. To insure that no precipitates form at the exit port 96 of the reactor 65, a heater 98 is positioned around the exit port 96 and in contact with the upper portion of the separation chamber 66. The heater 98 maintains the products of the chemical reaction in a gaseous state until these products are cooled by contact with water 100 in the separation chamber 66 as will now be described.

In accordance with the invention, the separation chamber 66 supports a movable absorber, such as water, in a position facing the exit port 96 so that the hot gasses resulting from the chemical reaction in the reactor 65 can be cooled, while the water absorbs the solid products which precipitate out from the chemical reaction during the cooling of the gasses. The water 100 is circulated by the pumps 76 from the reservoir 90 through an orifice 102 from which the water exits in the fashion of a miniature fountain directly beneath the exit port 96. The water covers the floor of the chamber 66 and flows through an exit pipe 104 and via a tee 106 back to the reservoir 90. The lower portions of the pipe 104 and the tee 106 are filled with water while the upper portions thereof are filled with gas whereby the gas is communicated via pipe 108 through the condenser 70 to the outlet 64 of the reactor system 50.

The walls of the chamber 66 are at a sufficient distance from the exit port 96 so that the products of the chemical reaction contact the water 100 prior to contacting a wall of the chamber 66. Thereby, the products of the chemical reaction are cooled by the water 100 resulting in the adsorption of any precipitates into the water prior to the contacting of a wall of the chamber 66 by the products of the chemical reaction. Contact by the water 100 with the hot products results in a heating of the water 100, this heat being removed by the chiller 74 and its refrigerant coil shown encircling the lower portion of the tee 106 as the water returns to the reservoir 90. Thereby, an accumulation of precipitate matter builds up in the reservoir 90, this accumulation being removed by opening the drain 92. In particular, it is noted that the precipitate accumulates slowly in the reservoir 90 so that, for example, the drain 92 need be opened only once every few months of continuous operation of the system 20. Excess heat of the gas passing through the pipe 108 is removed by the condenser 70 and the cooling fluid circulated therein by the coolant source 72. Thereby, the temperature of the gas at the outlet 64 is approximately room temperature, this being a suitable temperature for use of the analyzer 46.

In order to prevent contamination of the gas in the pipe 108 by any gasses which may be present in water, the water 100 is chemically pure and the circulation system for the water 100 is in the form of a closed circuit wherein the water 100 does not come in contact with the outside atmosphere. The reservoir 90 and the chamber 66 are filled with water by a procedure wherein the reservoir 90 and the chamber 66 are first cleared of all extraneous gasses by compressed nitrogen provided by the source 78 via the valve 80, the tank 86 and an inlet pipe 112. Thereafter, the valve 80 is closed and the valve 82 is opened to allow the compressed nitrogen to drive water from the tank 84 through the float valve 88 and the pipe 112 into the reservoir 90. As the water rises through the orifice 102 and the tee 106 into the chamber 66, the water also rises in the tank 86, the float of the float valve 88 being adjusted to close the valve 88 when the level of water 100 has reached the desired depth in the chamber 66. Any loss of water due to evaporation by the gaseous products of the chemical reaction is replaced by the float valve 88.

It is understood that the above described embodiment of the invention is illustrative only and that modification thereof may occur to those skilled in the art. Accordingly, it is desired that this invention is not to be limited to the embodiment disclosed herein but is to be limited only as defined by the appended claims.

What is claimed is:

1. A system for analyzing a material comprising:
   means for treating said material with a chemical reagent that reacts with inorganic carbonaceous substances in said material to produce a volatile compound of carbon;
   means coupled to said treating means for extracting said volatile compound from said material;
   means including a reactor coupled to said extracting means for heating said material in contact with a gaseous reagent to produce a chemical reaction resulting in a gaseous product and a precipitating product;
   means coupled to said heating means for measuring a quantity of said gaseous product;
   said heating means further including means for separating said gaseous product from said precipitating product, said separating means having a chamber positioned at an exit port of said reactor, a surface of said chamber including a movable absorber and wherein;
   said separating means includes means for projecting said absorber into said gaseous product for absorption of said precipitating product.

2. A system according to claim 1 wherein said projecting means comprises an orifice, said movable absorber is a liquid, and wherein said projecting means includes means for ejecting said liquid through said orifice.

3. A system according to claim 1 wherein said movable absorber is a liquid.

4. A system according to claim 3 further comprising means coupled to said chamber for moving said liquid through said chamber whereby said precipitating product is carried away from said chamber.

5. A system according to claim 4 wherein said moving means includes means for separating said liquid from the environment to prevent contamination thereby.

* * * * *